United States Patent [19]
Yakimicki et al.

[11] Patent Number: 5,472,445
[45] Date of Patent: Dec. 5, 1995

[54] DEVICE FOR MINIMIZING POROSITY IN BONE CEMENT UTILIZING CENTRIFUGATION AND VACUUM

[75] Inventors: Don Yakimicki, Plymouth; Kirt Case; Steve Hoag, both of Warsaw, all of Ind.

[73] Assignee: Zimmer, Inc., Warsaw, Ind.

[21] Appl. No.: 122,956

[22] Filed: Sep. 20, 1993

[51] Int. Cl.⁶ .............................. A61B 17/56; B04B 5/00
[52] U.S. Cl. ........................ 606/92; 494/32; 366/139
[58] Field of Search .................. 366/139; 494/32, 494/33, 39, 61; 606/92

[56] References Cited

U.S. PATENT DOCUMENTS

| | | | |
|---|---|---|---|
| D. 279,499 | 7/1985 | Case | D24/22 |
| 1,044,570 | 11/1912 | Raasloff et al. | 494/33 X |
| 2,453,914 | 11/1948 | Hollenback. | |
| 2,696,022 | 12/1954 | Steinbock et al. | |
| 2,777,177 | 1/1957 | Steinbock, Jr. | |
| 2,958,517 | 11/1960 | Harker et al. | |
| 2,973,187 | 2/1961 | Wehmer. | |
| 3,131,912 | 5/1964 | Steinbock, Jr. | |
| 3,343,817 | 9/1967 | Carangelo et al. | |
| 3,521,863 | 7/1970 | Graham. | |
| 3,603,564 | 9/1971 | Price et al. | |
| 3,610,586 | 10/1971 | Price et al. | |
| 3,640,510 | 2/1972 | Lea. | |
| 4,721,390 | 1/1988 | Lidgren | 366/139 |
| 4,758,096 | 7/1988 | Gunnarsson | 366/139 |
| 4,966,601 | 10/1990 | Draenert | 606/92 |
| 4,973,168 | 11/1990 | Chan | 366/139 |
| 5,100,241 | 3/1992 | Chan | 366/139 |

FOREIGN PATENT DOCUMENTS 4302230  8/1993  Germany .............................. 623/901

*Primary Examiner*—David H. Willse
*Attorney, Agent, or Firm*—Todd A. Dawson

[57] ABSTRACT

The mixing apparatus and method of this invention combines centrifugation and vacuum mixing to provide a device for the centrifugation of cement under a partial vacuum for the reduction of porosity within bone cement. The results of centrifugation under a vacuum are an improvement over the results achieved in standard centrifugation or standard vacuum mixing techniques. The device includes a receptacle which is spun rapidly about an axis under a partial vacuum. Creating a partial vacuum within the receptacle causes the air bubbles trapped within the cement to grow in size. The centrifugation causes the larger air bubbles to migrate through the cement toward the axis of rotation. Centrifugation works especially well under a partial vacuum due to the increased size of the air bubbles, in that larger bubbles migrate easier and quicker than smaller bubbles. Under centrifugation, the smaller air bubbles are compressed to such a degree that they become insignificant within the cement.

4 Claims, 3 Drawing Sheets

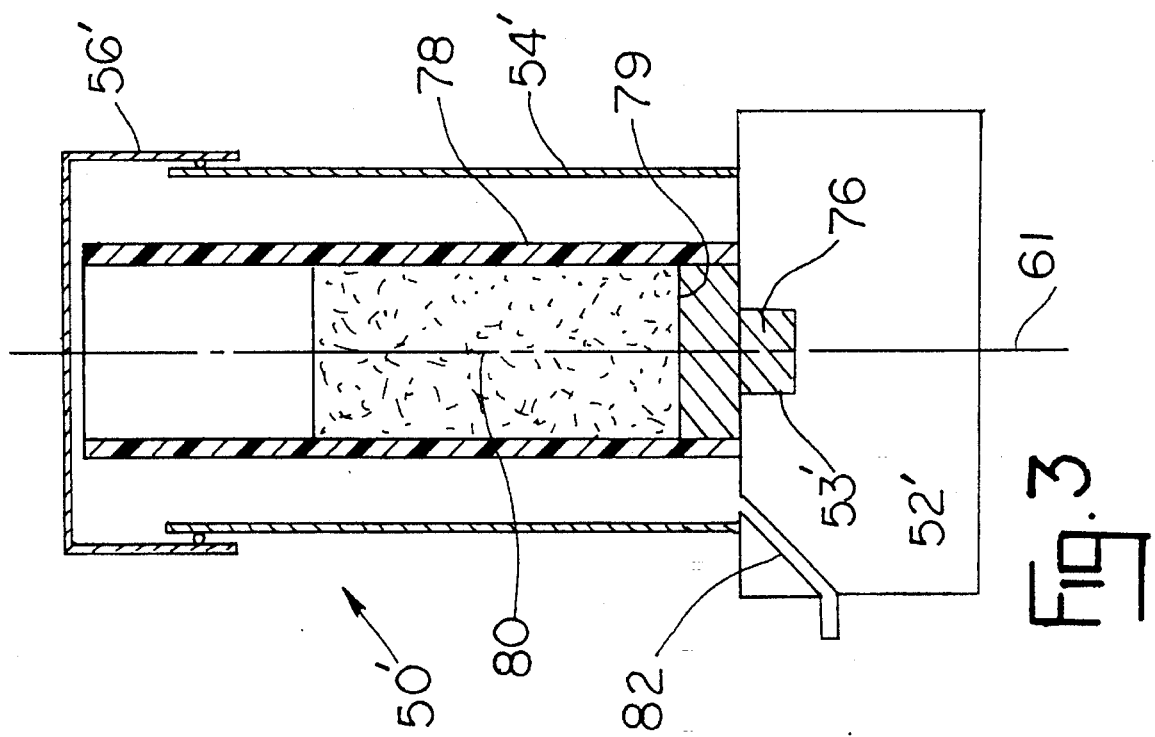
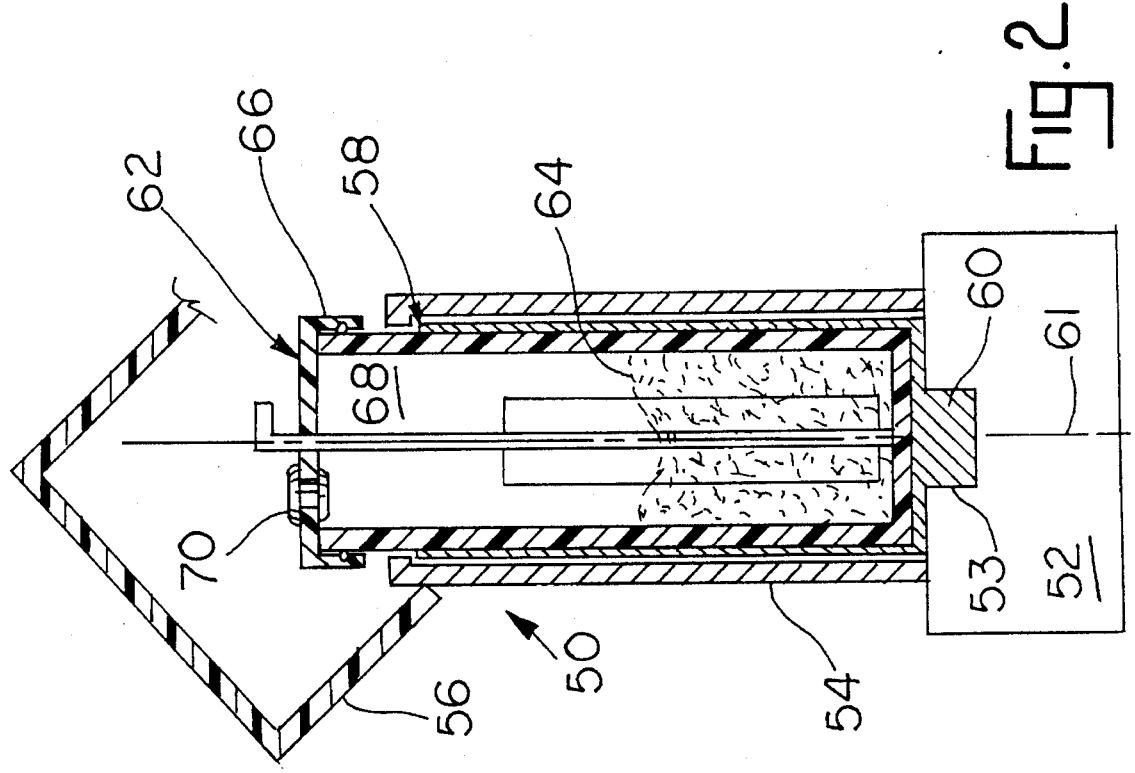

DEVICE FOR MINIMIZING POROSITY IN BONE CEMENT UTILIZING CENTRIFUGATION AND VACUUM

FIELD OF THE INVENTION

This invention relates to a system for the treatment of bone cement and has specific application to a device using centrifugation and vacuum for removal of air bubbles within the cement.

BACKGROUND OF THE INVENTION

Bone cement as used in orthopaedic surgery is formed from a liquid monomer and a powder polymer component which is mixed at the time of surgery. During the mixing process, air may be inadvertently introduced into the cement forming bubbles therein. Air bubbles within the cement may result in a decreased fatigue life for the cement.

Two basic methods have been developed aimed at limiting the amount of air bubbles remaining in the cement after mixing. First, numerous products have been developed for creating a partial vacuum during mixing under the theory that if the amount of air is reduced in the mixing chamber at the time of mixing, less can be introduced into the cement. Second, centrifugation has been used to rapidly spin the mixed cement such that any bubble trapped therein would migrate to the top of the container.

SUMMARY OF THE INVENTION

The mixing apparatus and method of this invention combines the two prior methods to provide a device for the centrifugation of cement under a partial vacuum. The results of centrifugation under a vacuum are an improvement over the results achieved in standard centrifugation or standard vacuum mixing techniques. The device includes a receptacle which is spun rapidly about an axis under a partial vacuum. Creating a partial vacuum within the receptacle causes the air bubbles trapped within the cement to grow in size. The centrifugation causes the larger air bubbles to migrate through the cement toward the axis of rotation. Centrifugation works especially well under a partial vacuum due to the increased size of the air bubbles, in that larger bubbles migrate easier and quicker than smaller bubbles. Under centrifugation, the smaller air bubbles are compressed to such a degree that they become insignificant within the cement.

Accordingly, it is an advantage of the invention to provide for an apparatus for centrifugation of mixed cement under a partial vacuum for the reduction of air bubbles trapped therein.

Another advantage of the invention is to provide for a novel method of limiting the amount of air bubbles contained within bone cement.

Another advantage of the invention provides for drawing a vacuum on a container of bone cement during centrifugation for the reduction of porosity of the bone cement.

Still other advantages of the present invention will become apparent upon a reading of the following description taken with the accompanying drawings.

BRIEF DESCRIPTION OF THE DRAWINGS

FIG. 2 is a diagrammatical view of a second embodiment of the invention.

FIG. 3 is a diagrammatical view of an alternative to the second embodiment of the invention.

DESCRIPTION OF THE PREFERRED EMBODIMENTS

The preferred embodiments herein described are not intended to be exhaustive nor to limit the invention to the precise forms disclosed. Rather, they are chosen and described to best explain the invention so that others skilled in the art might utilize their teachings.

Figure 1:
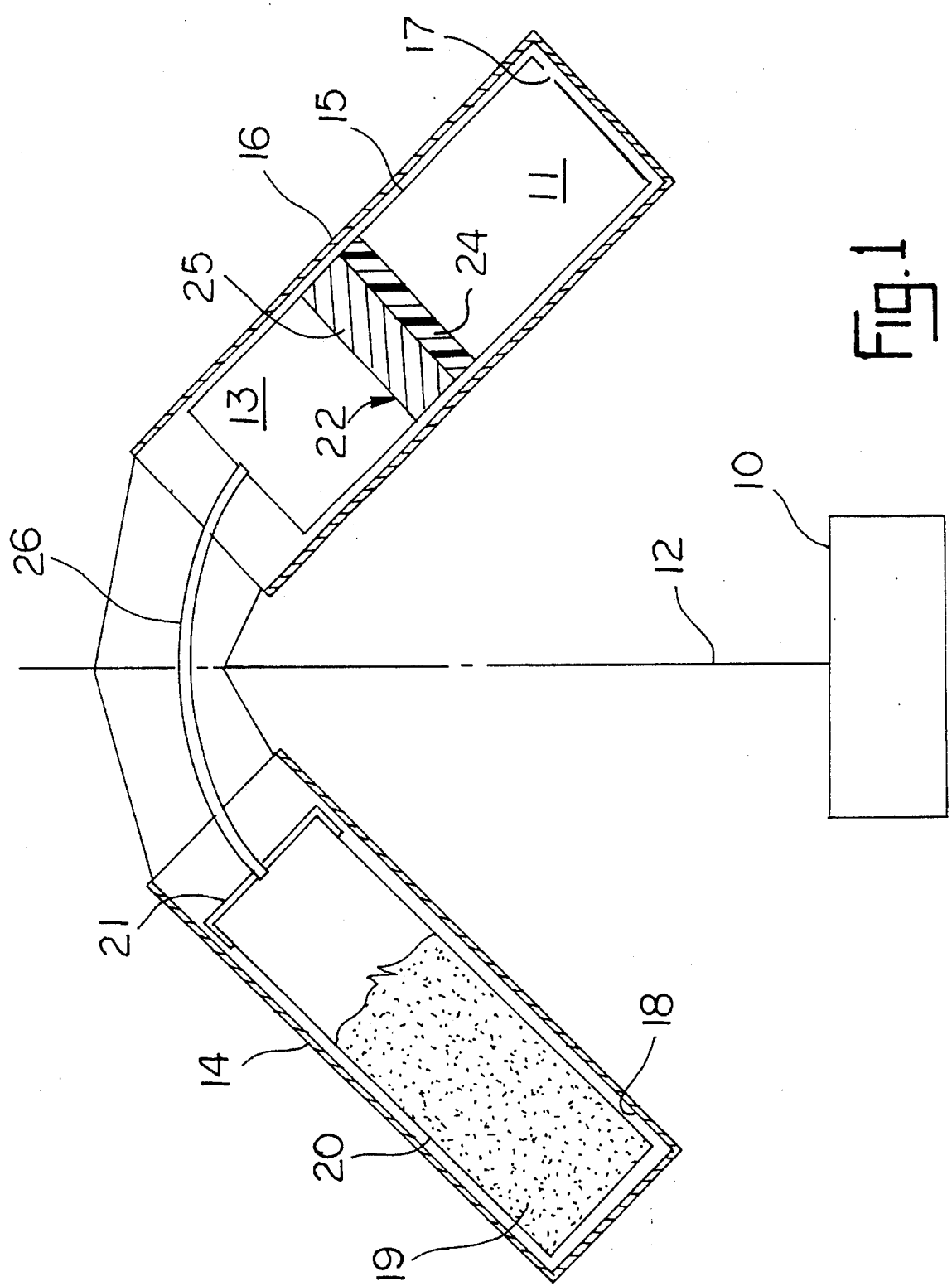
FIG. 1 is a diagrammatical view illustrating one embodiment of the invention for subjecting the mixed cement to a vacuum and centrifuge for the removal of air bubbles within the cement.

Referring now to FIG. 1, the invention is illustrated in diagrammatical form and includes a centrifuge motor 10 having a central shaft 12 defining the axis of rotation for the motor 10. A pair of cylinders 14, 16 are connected to the central shaft 14 in a known manner so that the cylinders 14, 16 are secured to the shaft during rotation of the shaft by motor 10. Cylinder 14 is open at the top and defines an interior space 18 for accommodating a cement cartridge 20. A cap 21 is hermetically connected to the cartridge 20 by known means such as screw threads and O-rings (not shown). Cylinder 16 defines an interior space 20 for accommodating cartridge 15. Cartridge 15 is cylindrical in shape and includes closed ends. A weighted plunger 22 is carried within cartridge 15 and includes a plunger part 24 forming a hermetic seal with the interior of the cylinder walls and a weight part 25 carried by the plunger part. The weighted plunger divides the cylinder into upper area 13 and lower area 11. The upper area 13 is sealed and the lower area 11 is vented through port 17 to the ambient atmosphere. An air tube 26 is connected to cap 21 and the upper area 13 of cylinder 16 and places cartridges 15 and 20 in air flow communication.

In use, a cement cartridge 20 having a quantity of mixed bone cement 19 therein is placed within cylinder 14 as illustrated. Cap 21 is placed on cartridge 20. Cap 21 includes a sealing member such as an O-ring (not shown) to seal the interior of the cartridge from the ambient atmosphere. With the weighted plunger 22 positioned at or near the top of cartridge 15 within area 13, motor 10 is turned on to rotate shaft 12 and thereby cylinders 14 and 16 about the shaft. As the cylinders rotate with shaft 12, centrifugal force pulls weighted plunger 22 toward the lower area 11 of cartridge 15. As the plunger travels within the cylinder, it creates a partial vacuum within the upper area 13 of the cartridge. Air is exhausted out of the lower area 11 through vent 17. The vacuum within the upper area 13 of cartridge 15 pulls air from cartridge 20 through tube 26 to create a partial vacuum within the interior of cartridge 20. The partial vacuum within cartridge 20 causes a reduced pressure within cement 19 thereby expanding any air bubbles trapped therein. In essence, the partial vacuum causes some air bubbles to grow under the reduced atmosphere. Continued centrifugation of the cylinders causes the cement around the air bubbles to settle, thereby migrating the bubbles out of the cement. The centrifugation causes smaller air bubbles to become compressed under centrifugal force. As the motor, shaft, and cylinders continue to rotate, the weighted plunger continues to draw an increased vacuum within cartridge 20 so long as weighted plunger 22 is not in contact with the bottom of cartridge 15. In the preferred embodiment the volume of the cylinders will be matched such that weighted plunger 22 will be suspended near or slightly below the midpoint of cartridge 15 to ensure an adequate vacuum during centrifugation.

After a predetermined period of time, the motor is turned off and cartridge 20 is removed and placed within an appropriate cement injection gun (not shown) for application of the cement. The simultaneous combination of centrifugation and vacuum treatment of bone cement yields a bone cement having an increased fatigue cycle and lower porosity than cement treated by only one of the methods alone. It may be advantageous to provide a spring (not shown) within the lower area 11 to bias the weighted plunger 22 toward upper area 13 when the motor is turned off to assist in resetting the device.

A second embodiment of the invention is illustrated in diagram form in FIG. 2. The centrifugation/vacuum treatment device 50 of FIG. 2 includes a motor 52 having a central recess 53 exposing driving gears (not shown). An outer cylinder 54 extends from the motor as shown and includes a cap 56 hinged to the cylinder and configured to enclose the upper end of the outer cylinder 54. Outer cylinder 54 is fixed to the motor 52 and forms a protective sleeve. An inner cylinder 58 is positioned within outer cylinder 54 and includes a protrusion 60 which is accommodated by the central recess of motor 52. The upper end of inner cylinder 58 is open. When motor 52 is turned on, inner cylinder 58 is engaged at protrusion 60 by the motor's gears (not shown) and rotated about the central axis 61 of device 50.

In use, a cement cartridge 62 having a quantity of mixed cement 64 carried therein is placed within inner cylinder 58. Cylinder 58 makes frictional contact with cartridge 62. Cartridge 62 includes a cap 66 affixed thereto and defining a sealed interior space 68. A resilient plug 70 is positioned within an opening formed in cap 66 and forms an airtight seal with the opening. The cement cartridge 62 is a known device of the type illustrated in U.S. Pat. No. 5,100,241 issued to Kwan-Ho Chan on Mar. 31, 1992, and incorporated herein by reference. During the mixing process, a needle device is inserted through plug 70 and a partial vacuum is drawn within the cement cartridge. A more complete description of the process of mixing the cement under pressure can be had by a reading of the incorporated reference. It is assumed for this purpose that the partial vacuum still exists within the cement cartridge 62.

After the cement cartridge is positioned within the inner cylinder 58, cap 56 on outer cylinder 54 is closed. Motor 52 is turned on and through its drive gears (not shown) begins to rotate inner cylinder 58 at a high speed. With the cement cartridge 62 in frictional engagement with inner cylinder 58 as the inner cylinder rotates about the central axis 61 of device 50 so does cement cartridge 62. It should be noted that outer cylinder 54 is provided to protect the user from the inner cylinder 58 and cement cartridge 62 which rotate at a high speed. As the cement cartridge rotates about axis 61, the cement 64 is urged by centrifugal force toward the side walls of cartridge 62 so that air bubbles trapped therein will migrate toward the center of the cartridge. As with the first embodiment, the device 50 of FIG. 2 utilizes a partial vacuum in simultaneous combination with centrifugation to minimize the porosity of the cement caused by air bubbles. The vacuum within the cartridge causes some air bubbles to expand due to a reduced pressure within the cartridge. Centrifugation of the cement is more effective with larger air bubbles than with smaller air bubbles. Further, smaller air bubbles are compressed by weight of the cement under centrifugation. Therefore, the porosity of the cement caused by air bubbles is minimized using the combination of vacuum and centrifugation.

An alternative device 50' of the second embodiment of FIG. 2 is illustrated in diagram form in FIG. 3. Device 50' included a motor 52' having a central recess 53' exposing drive gears (not shown). A fixed outer cylinder 54' includes an open end. A cap 56' is connectable to cylinder 54' with sealing member such as O-ring positioned therebetween to seal the interior of the cylinder. To provide a total interior seal of cylinder 54', motor 52 should be provided with vacuum sealed bearings (not shown) about the central recess of the motor. A spindle 76 is positioned within the central recess of the motor for rotation by the motor. A portion of spindle 76 extends upwardly from motor 52'. A cement cartridge 78 having a lower end defining a cavity 79 for accommodating a portion of spindle 76 is provided and carries a quantity of mixed cement 80. The upper end of the cartridge 78 is open. A vacuum port 82 extends through the housing of the motor and communicates between the interior space defined by cylinder 54' and the exterior of the motor as shown.

In use, a pump (not shown) is connected through tubing (also not shown) to vacuum port 82 to draw air from within the interior of cylinder 54'. Motor 52' is turned on and begins to rotate spindle 76 and cement cartridge 78 about the central axis 61' of the device 50'. Since cartridge 78 is open to the interior of cylinder 54', the vacuum created in cylinder 54' affects the cement carried by the cartridge in the same manner as described with the previous embodiments. The partial vacuum reduces the ambient pressure about the cement thereby causing the air bubbles trapped therein to enlarge. The centrifugation in combination with the vacuum enables the enlarged air bubbles to migrate toward the center of the cartridge and be drawn out of the cement. Bubbles still too small to migrate out of the cement may be compressed by the centrifugal force of the cement.

Figure 4:
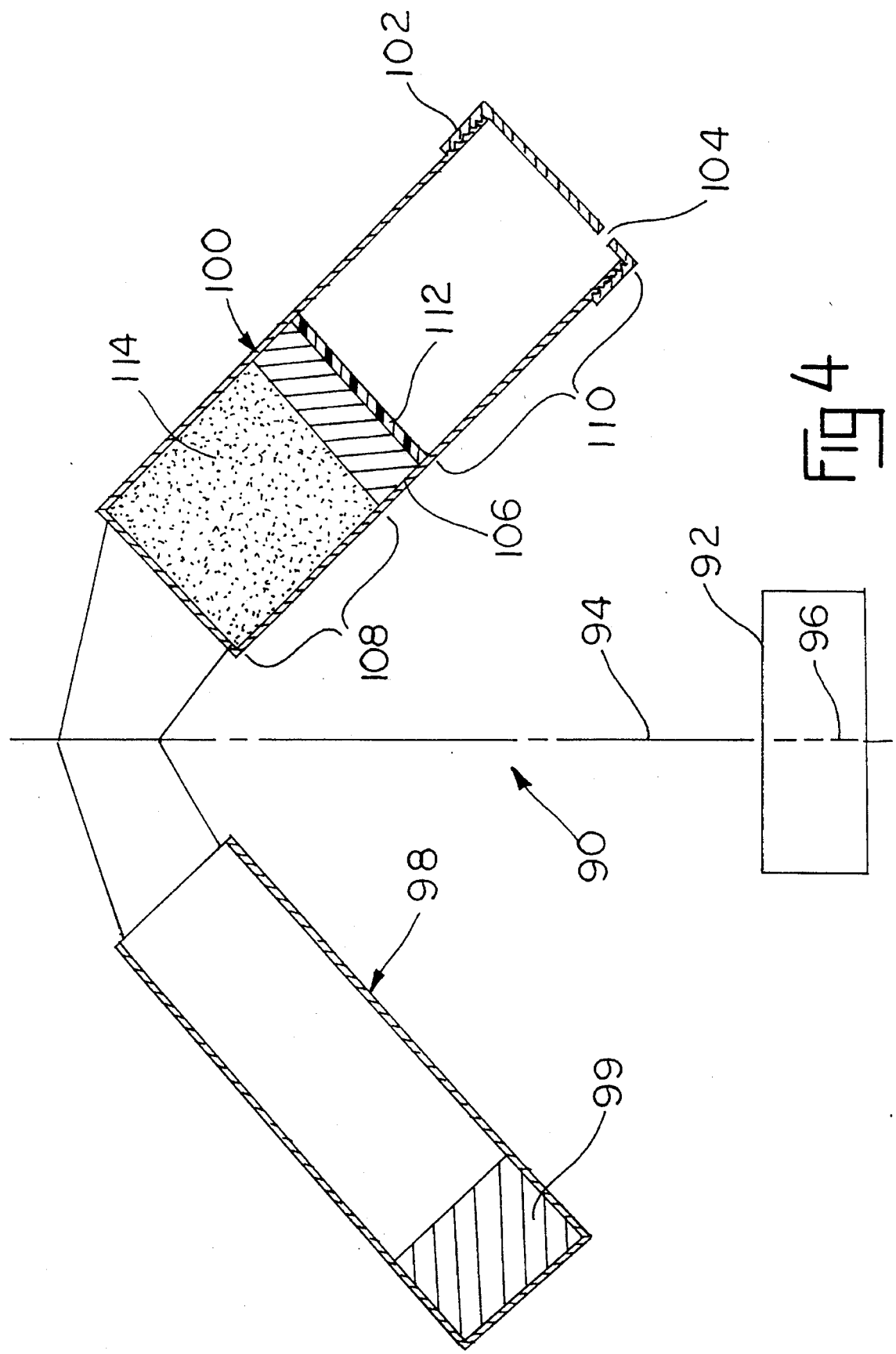
FIG. 4 is a diagrammatical view of a third embodiment of the invention.

A third embodiment of the invention is illustrated in FIG. 4 in diagrammatical form. Device 90 includes a motor 92 having a rotatable shaft extending upwardly therefrom aligned with the motor's central axis 96. A pair of cylinders 98, 100 are suspended from shaft 94 in a manner common with centrifuge devices. Cylinder 100 included an open end having external threads thereon for accommodating a cap 102 as shown. A vent opening 104 is formed through cap 102. A weighted plunger 106 is slidably carried within cylinder 100 and divides the interior into an upper area 108 and a lower area 110. Plunger 106 includes a gasket 112 which forms an airtight Seal with the side walls of the cylinder. Cylinder 98 merely includes a weight 99 and is provided as a counterbalance against cylinder 100.

In use, prior to connection of cylinder 100 to shaft 94, a quantity of mixed bone cement 114 is poured into upper area 108 of cylinder 100. Weighted plunger 106 is placed in contact with the quantity of bone cement 114 as shown. Gasket 112 forms a hermetic seal with the interior wall of the cylinder. Cap 102 is secured to cylinder 100 and the cylinder is attached to shaft 94. Motor 92 is turned on to rapidly rotate cylinders 98 and 100 about shaft 94. Centrifugal force causes weighted plunger 106 to slide toward cap 102. Since the plunger forms a seal with the cylinder's wall as the plunger slides toward cap 102, the upper area 108 is expanded without the introduction of additional air within the area thereby creating a reduced atmosphere within area 108. The reduced atmosphere causes the air bubbles within the cement to expand and migrate out of the cement under centrifugation. Smaller bubbles are compressed during centrifugation. The advantage of this embodiment is that the device 90 creates its own reduced atmosphere or partial vacuum without additional pumps or components.

It should be understood that the invention should not be limited to the precise forms disclosed but may be modified within the keeping of the amended claims.

We claim:

1. A device for minimizing the porosity in bone cement caused by air entrapped in the cement, the device including a cylinder configured to hold a predetermined quantity of uncured bone cement, the cylinder being configured for placement within a cement delivery device, a motor means connected to the cylinder for rotating the cylinder about a central axis, and vacuum means operatively associated with the cylinder for creating a vacuum within the cylinder as the motor means rotates the cartridge about the central axis, wherein the vacuum means includes a second cylinder and a weighted plunger, the second cylinder being connected to the motor means, the plunger being shiftable within the second cylinder and forming an airtight seal with interior sidewalls of the second cylinder, the second cylinder having a first end which is vented to ambient atmosphere and a second end which is in air flow communication with the first mentioned cylinder, said plunger being shiftable from a first position adjacent the second end and a second position adjacent said first end as said motor rotates the first and second cylinder to create a vacuum in said first cylinder.

2. A device for minimizing the porosity in bone cement caused by air entrapped in the cement, the device including a first cylinder configured to hold a predetermined quantity of uncured bone cement, the first cylinder being configured for placement within a cement delivery device, a motor means connected to the first cylinder for rotating the first cylinder about a central axis wherein the first cylinder is positioned radially to the central axis, and vacuum means operatively associated with the first cylinder for creating a vacuum within the first cylinder as the motor means rotates the first cylinder about the central axis, the vacuum means including a second cylinder and a weighted plunger, the second cylinder being connected to the motor means, the plunger being shiftable within one of said first and second cylinders and forming an airtight seal with interior sidewalls thereof, each of the first and second cylinders having a first end and a second end, said plunger being shiftable from a first position adjacent the first end and a second position adjacent said second end as said motor rotates the first and second cylinder to create a pressure less than ambient adjacent said first end.

3. The device of claim 2 wherein the plunger is carried within said second cylinder, the first end of the second cylinder being connected in flow communication with the first cylinder, the second end of said second cylinder including a vent, and as said plunger shifts from its first position toward its second position the plunger creates a pressure less than ambient in the first ends of the first and second cylinders.

4. The device of claim 2 wherein the plunger is carried within the first cylinder adjacent a quantity of uncured bone cement carried within the first cylinder adjacent the first end, the second end of the first cylinder including a vent, and as said motor rotates the first and second cylinder, the weighted plunger is shifted from a position adjacent the first end toward a position adjacent the second end thereby creating an area of reduced atmosphere adjacent the first end of the first cylinder, wherein the quantity of uncured bone cement carried within the first cylinder is subjected to the reduced atmosphere.

* * * * *